United States Patent [19]
Rousseau

[11] Patent Number: 5,428,987
[45] Date of Patent: Jul. 4, 1995

[54] DEVICE FOR MEASURING THE POROSITY OF A FILTER ELEMENT

[75] Inventor: Alain Rousseau, Orleans, France

[73] Assignee: Societe Nationale d'Exploitation Industrielle des Tabacs et Allumettes, France

[21] Appl. No.: 216,993

[22] Filed: Mar. 24, 1994

[30] Foreign Application Priority Data

Mar. 26, 1993 [FR] France .................. 93 03799

[51] Int. Cl.⁶ .................................. G01N 15/08
[52] U.S. Cl. .................................. 73/38
[58] Field of Search .................................. 73/38

[56] References Cited

U.S. PATENT DOCUMENTS

| | | | |
|---|---|---|---|
| 4,069,704 | 1/1978 | Grant, Jr. et al. | 73/38 |
| 4,246,774 | 1/1981 | Flesselles et al. | 73/38 |
| 4,627,448 | 12/1986 | Kamm et al. | 73/38 |
| 4,912,964 | 4/1990 | Ohtsuki et al. | 73/38 |

FOREIGN PATENT DOCUMENTS 0007836 6/1980 European Pat. Off. .
2019190 10/1978 United Kingdom .

*Primary Examiner*—Hezron E. Williams
*Assistant Examiner*—Michael J. Brock
*Attorney, Agent, or Firm*—William A. Drucker

[57] ABSTRACT

The device embodying the invention uses a filter element encapsulating means acting like a sphincter, a means enabling an air flow to be generated through the filter element once the filter element has been encapsulated, and a means enabling measurement of at least one parameter relating to the fluid flow through the filter. The encapsulating means comprises a succession of encapsulation modules arranged coaxially end to end and each acting like a sphincter, independently of the others, by means of a control means separate from that of the others. The invention applies notably to the measurement of draw through the filter sticks used in filter-tipped cigarettes.

12 Claims, 3 Drawing Sheets

DEVICE FOR MEASURING THE POROSITY OF A FILTER ELEMENT

BACKGROUND OF THE INVENTION

1. Field of the Invention

This invention relates to a device for measuring the porosity of a filter element in the form of a substantially cylindrical-shaped rod or stick.

It applies notably, though not exclusively, to the measurement of draw through filter sticks used in filter-tipped cigarettes.

2. Description of the Prior Art

For this type of application, an encapsulation device has already been proposed using a rigid tubular element whose inner wall is lined with an elastic tubular membrane attached by its end edges to the two ends of said element so as to delimit an intermediate volume in which a partial vacuum can be created.

The cross section delimited by the membrane at rest is provided substantially equal to that of the filter to be measured, and slightly smaller than that of the tubular element.

In this way, the creation of a partial vacuum in the intermediate volume causes a retraction of the membrane which tends to apply itself against the inner wall of the tubular element. Accordingly, the cross section delimited by the membrane becomes greater than that of the filter which can thus fit unhindered into the assembly constituted by the two parts.

Once the filter has been disposed inside this assembly, the intermediate volume is returned to atmospheric pressure. The tubular membrane then spreads out like a sphincter, under then effects of its own elasticity, to apply itself against and "encapsulate" the filter.

The porosity or draw of the filter can then be determined by creating a partial vacuum at one of the orifices of the tubular element while the other one is left unconnected, and by taking e.g. a measurement of the pressure at a constant flow rate of the air sucked through the filter.

In order to enable filter elements of different lengths to be measured using a structure of this type, it has been proposed to adjust the useful length of the flexible membrane by means of a tubular sleeve susceptible of axial sliding inside the membrane so as to confine the expansion of the membrane over part of its length. The dimensions of this sleeve are provided so that, in this part, the diameter of the sphincter will be greater than that of the filter.

It so happens that a device of this type has a certain number of drawbacks.

Firstly, adjustment of the encapsulation length, which can be performed continuously, can only be performed in the control mode.

Moreover, it is difficult to automate the positioning of the tubular sleeve as a function of the length of the filter, as this would require a relatively complex tube displacement system and system for measurement thereof.

Furthermore, this device is necessarily cumbersome in terms of height since, in order to measure a filter encapsulated over its maximum length, the tube must be completely removed from the tubular membrane, thereby increasing the total height of the measurement head by said length.

It has also been observed that, in a same draw measurement cycle, it is not possible to successively measure the filter with total encapsulation and the filter with partial encapsulation in order to obtain a parameter depending on the porosity of the filter jacket.

OBJECT OF THE INVENTION

The main object of this invention is to remedy the preceding disadvantages.

SUMMARY OF THE INVENTION

Accordingly, there is provided a device for measuring the porosity of a filter element, said device using a filter element encapsulating means acting like a sphincter, a means enabling an air flow to be generated through the filter element once the filter element has been encapsulated, and a means enabling measurement of at least one parameter relating to the fluid flow through the filter.

According to the invention, this device is characterized in that the encapsulating means comprises a succession of encapsulation modules arranged coaxially end to end and each acting like a sphincter, independently of the others, by means of a control means separate from that of the others.

It is obvious that, by way of such an arrangement, it becomes possible to vary the encapsulation height and to adapt it to the length of the filters by modifying the number of modules activated.

Each encapsulation module can comprise a tubular or possibly cylindrical body whose inner cylindrical wall is lined with an elastic tubular membrane which, along with said wall, delimits an intermediate volume in which the pressure can be modified by a control circuit so that said membrane can be in the following two states:

- a retracted state, retracted towards said wall and providing a cross section of maximum passage,
- an out-spread state, spread out towards the center of the body, in which it has a cross section of reduced passage, so as to be able to apply itself against and partially encapsulate a filter element previously disposed inside the body.

Switching from one state to the other can, of course, be performed by admission of a pressurized fluid or, conversely, by creation of a partial vacuum in the intermediate volume, with return to the initial position taking place by way of the elasticity of the membrane.

According to another embodiment of the invention, the encapsulating means comprises a single body whose inner wall is lined with a succession of membrane portions connected end to end to one another, in a tight manner, by means of a multiplicity of elastic annular distance tubes in airtight contact with said body, so as to constitute a succession of intermediate volumes each delimited by the inner wall of the body, a membrane portion and two successive annular distance tubes, each of these volumes being connected to a control circuit separate from that of the others.

BRIEF DESCRIPTION OF THE DRAWINGS

Further features and advantages of the invention will be apparent from embodiments of the invention described, by way of non-limiting examples, in reference to the corresponding accompanying drawings in which.

DESCRIPTION OF THE PREFERRED EMBODIMENTS

Figure 2:
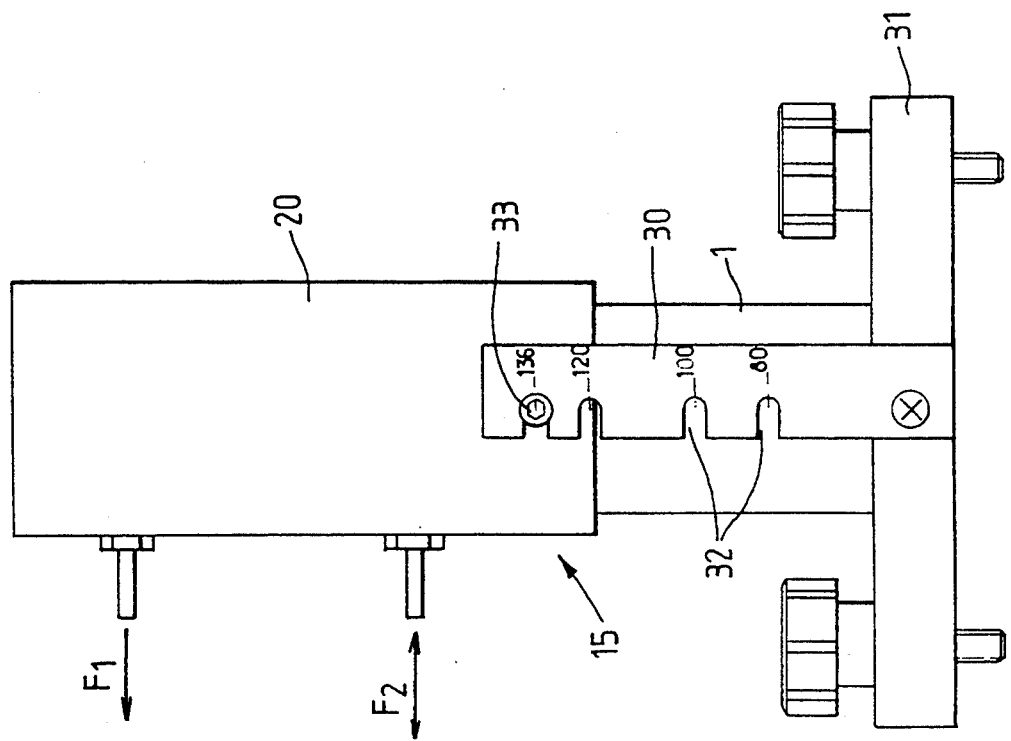
FIGS. 1 and 2 are respectively an axial cutaway view and an upright projection of a measurement head for measuring the draw of cigarette filters, with manual adjustment of the encapsulation height.
Figure 1:
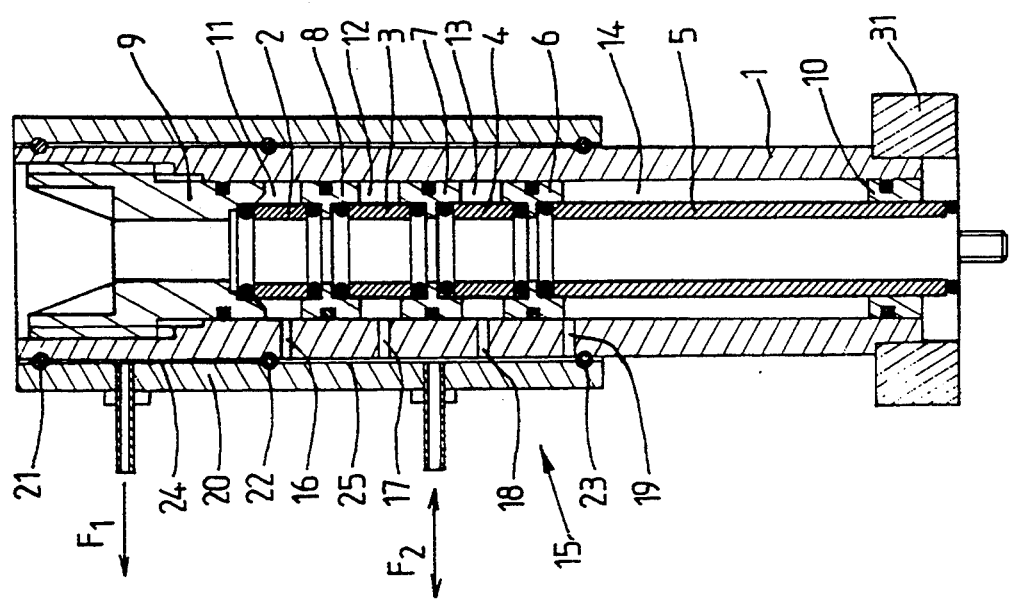

As represented in FIG. 1, the measurement head comprises a substantially cylindrical tubular body 1 inside which are arranged, end to end, plural coaxial tubular membrane portions 2, 3, 4, 5 connected to one another in an airtight manner by means of annular distance tubes 6, 7, 8, 9, 10 attached in an airtight manner to the body 1. In this instance, the tightness of the distance tube/membrane/body is achieved with O-ring seals.

These distance tubes 6 to 10 delimit, along with the membrane portions and the body, intermediate chambers 11, 12, 13, 14 which communicate with a distributor 15 associated with the body 1 via radial bores 16, 17, 18, 19.

In this example, the distributor consists of a slide valve formed by a cylindrical tubular sleeve 20 mounted slidably on the body 1 by means of three tightness seals 21, 22, 23 axially offset so as to delimit two annular chambers 24, 25 of which one is connected to a permanent suction circuit (arrow F1), with the other being connected to a control circuit (arrow F2) capable of generating a suction or an airing, or even an injection of pressurized fluid.

The lower membrane portion 5 or basic sphincter is of height equal to the shortest length of the filter. Subsequent to a suction in the chamber 14, it is in the retracted state to enable a filter stick to be inserted, and then ejected. It moves into the outspread state (airing or pressurizing of the chamber) to encapsulate the filter during the draw measurement process.

The upper membrane portions 2, 3 and 4 are intended to be maintained retracted, by a permanent suction in the chambers 11, 12, 13, or simultaneously commanded with the basic sphincter 5, as a function of the length of the filter stick.

In order to facilitate the adjustment process as a function of this length, the distance axially separating the two seals 22, 23 is slightly greater than the distance included between the bores 16 and 19 so that, in the upper position of the sleeve 20, the four bores 16, 17, 18, 19 open into the chamber 25. The lower position of the sleeve 20 is such that only bore 19 communicates with the chamber 25. The distance separating the seals 21, 22 is designed such that, in the lower position of the portion, the bores 16, 17 and 18 open into the chamber 24.

For instance, the membrane portions 5, 4, 3, 2 can respectively have lengths of 80 mm, 20 mm, 20 mm and 16 mm, for filter sticks 80 mm, 100 mm, 120 mm and 136 mm long.

In order to measure a filter stick 80 mm long, the tubular element 20 will be placed in the lower position so that only bore 19 communicates with the chamber 25 and so that only the basic sphincter 5 is in the out-spread position during measurement.

In order to measure a filter stick 120 mm long, the tubular element will be brought to the intermediate position so that the bores 17, 18 and 19 communicate with chamber 25 and so that the membrane portions 5, 4, 3 can take up an outspread position during the measurement.

In order to measure a filter stick 136 mm long, the tubular element 20 will be brought to the upper position so that all the bores 16 to 19 communicate with the chamber 25 and so that the membranes 2 to 5 are controlled synchronously.

A meter rule 30 comprising notches 32 corresponding to each measurement position is fixed to the base 31 supporting the body 1.

The tubular element 20 comprises a snug 33 that can latch into each of these notches 32 so as to be retained in the axial position required for the measurement envisaged.

The position of the tubular element 20 is adjusted by rotation about its main axis by a value sufficient to disengage the snug 33 from the notch 32 in which it had been inserted, and then, after a translation in the required direction, repositioning of the snug 33 in the notch corresponding to the adjustment required by a further rotation of the sleeve 20 in the opposite direction.

The invention is not, of course, limited to the embodiment previously described.

Figure 3:
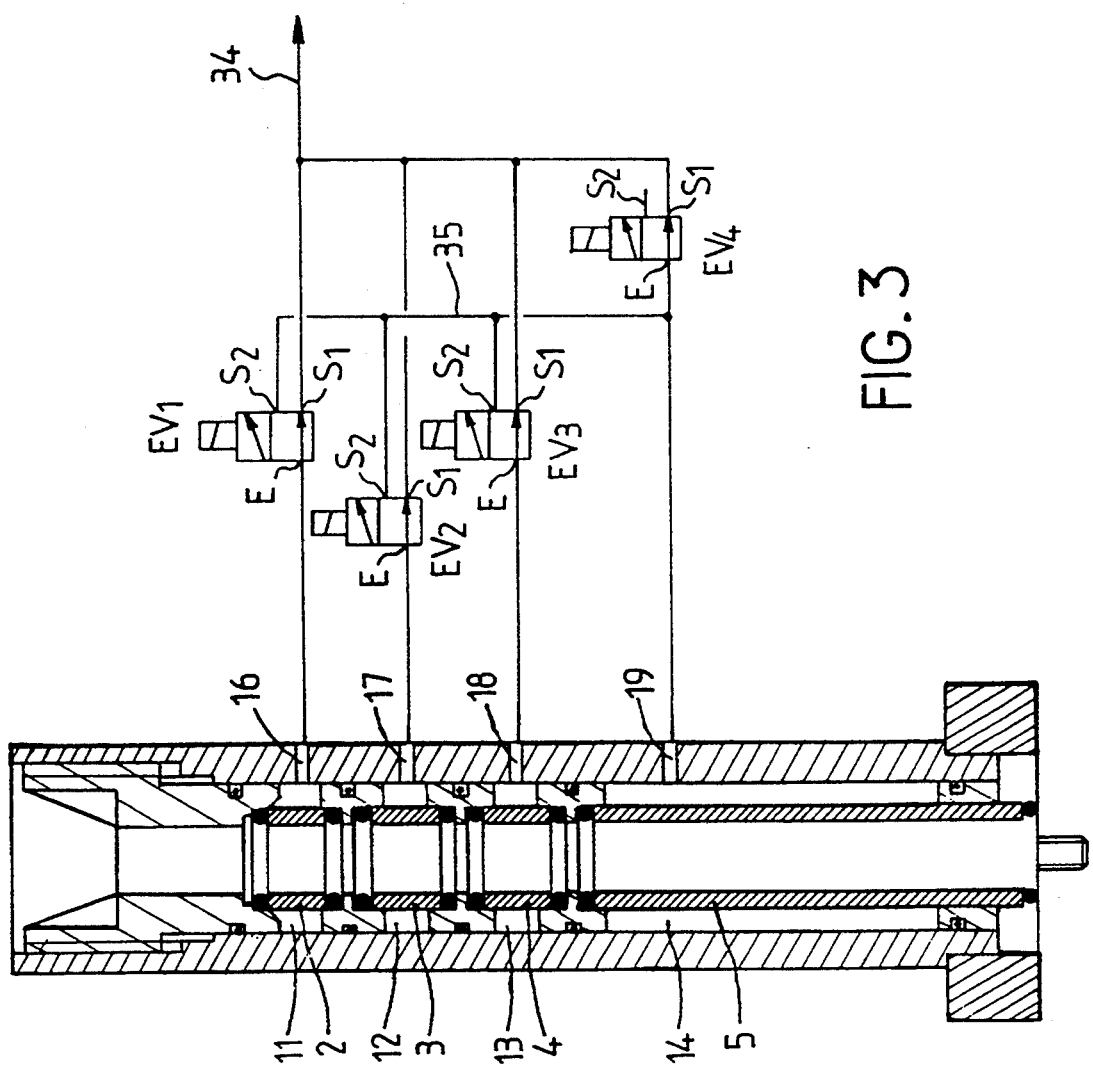
FIG. 3 is an axial cutaway view of a device of similar type to that of FIG. 1 but in which the adjustments are ensured by an automatable control circuit.

In this way, instead of using a distributor of the slide valve type, the encapsulation head could be associated with a distribution circuit commanded by electrovalves, such as the one represented in FIG. 3.

In this example, the bores 16, 17, 18, 19 made in the body 1 are connected to four respective electrovalves $EV_1$ to $EV_4$ whose direct outputs $S_1$ are connected to a permanent suction circuit 34. The derivation outputs $S_2$ of the electrovalves $EV_1$ to $EV_3$ are connected to the input of the electrovalve $EV_4$. The derivation output $S_2$ of the latter leads to the outside (atmosphere) or even into a pressurized fluid admission circuit.

This distribution circuit then operates as follows:

In order to enable the filter stick to be inserted, the electrovalves $SV_1$ to $SV_4$ are commanded so as to take on their position in FIG. 3, in which the input E is connected to the direct output $S_1$, so that the intermediate chambers 11 to 14 are subjected to a permanent suction. The membrane portions 5 to 2 are therefore in the retracted position, thus providing a cross section of passage greater than the cross section of the filter stick.

Encapsulation will then take place by switching at least the electrovalve $EV_4$ and, depending on the length of the stick, one or more of the next electrovalves $EV_3$, $EV_2$, $EV_1$.

By way of this switching, the inputs E of the switched electrovalves are connected to the derivation output $S_2$ thereof and therefore to the derivation circuit 35 (or to the pressurized fluid circuit, as the case may be) which is aired by the output $S_2$ of the electrovalve $EV_4$.

The membrane portions corresponding to the electrovalves that have been switched change to the outspread state while encapsulating the filter stick, while the other membrane portions remain in the retracted state.

Once the draw has been measured, the ejection phase is obtained by returning the electrovalves $EV_1$ to $EV_4$ to their initial state so as to have the membrane portions 2 to 5 retract.

The stick that has just been tested can then be removed, e.g. by letting it descend by gravity.

An important advantage of the device previously described consists in that it enables determination of the porosity of the jacket, e.g. paper jacket, of the filter sticks.

In this case, two consecutive measurements must be performed, i.e.

a measurement of standardized draw, TFE, performed with complete encapsulation of the filter stick, and a measurement, TPE, which is performed with partial encapsulation so as to integrate a factor pertaining to the porosity of the jacket paper.

In the case of the filter stick tested comprising a nonporous jacket, the air flow passing through the filter during a TPE measurement will, of course, be identical to the reading taken during the TFE measurement.

Conversely, in the case of a filter stick with a porous jacket, the TPE measurement will differ from the TFE measurement due to the sucked air flow laterally penetrating inside the filter, via the jacket. The difference between these two readings thus represents the porosity of the jacket.

In practice, a nominal value established beforehand for the TPE measurement will be defined in the filter stick specifications. During production inspections, it will then be possible to check that the TPE value measured corresponds to the nominal value, and thus to control the porosity of the jacket used, in addition to the measurement of the draw of the fully encapsulated filter.

Figure 4:
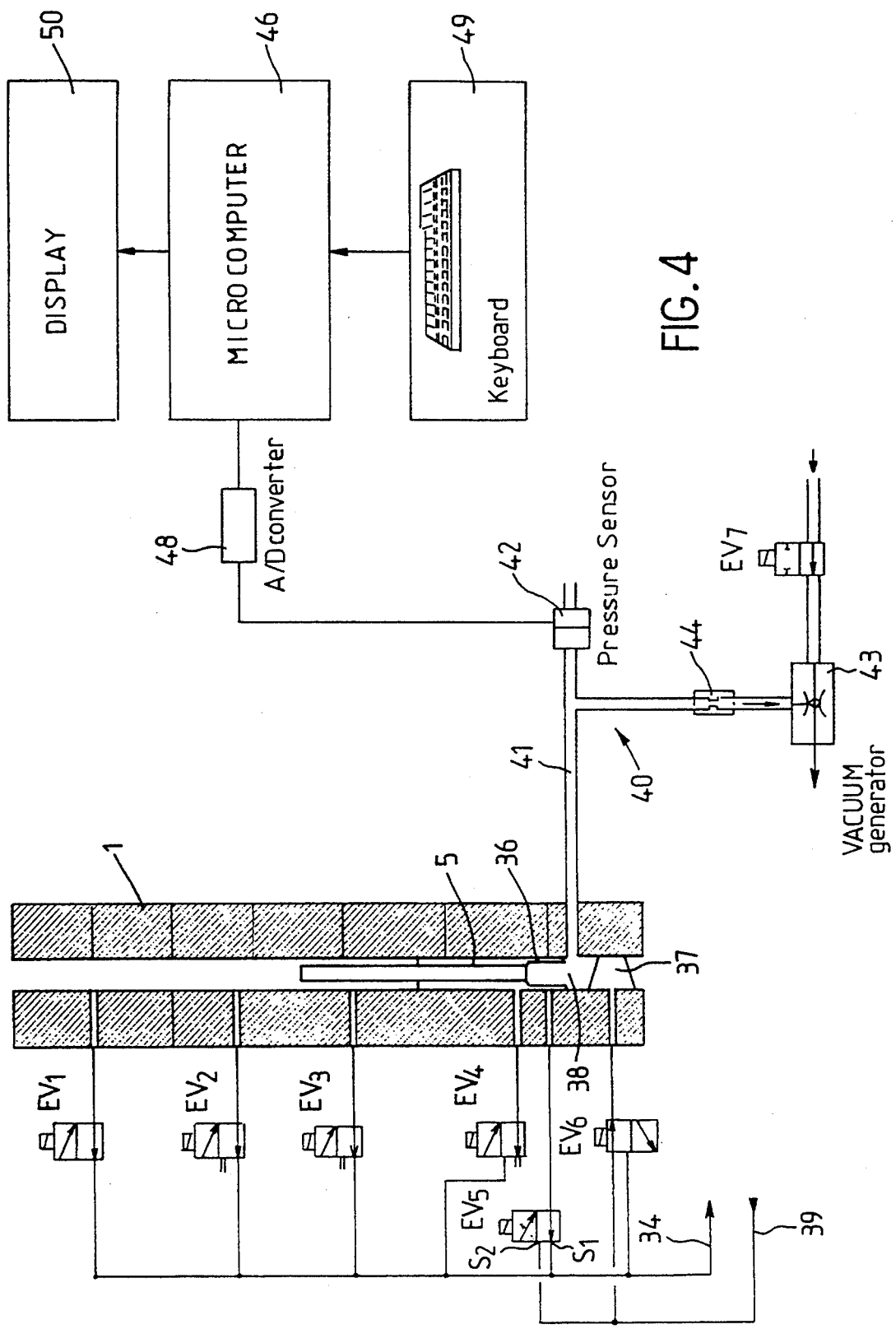
FIG. 4 is a schematic representation of an installation for automatic measurement of the draw of the cigarette filters.

The installation represented in FIG. 4 uses an encapsulation head of the type of the one represented in FIG. 3 and with which is associated a distribution circuit comprising four control electrovalves $EV_1$ to $EV_4$.

Furthermore, this encapsulation head successively comprises the following elements, housed in the tubular body 1 below the basic sphincter 5:

an elastic membrane portion 36 forming an additional sphincter acting as a retaining stop for the filter stick when the latter is inserted, an expandable sealing shutter 37 comprising an elastically deformable pocket commanded pneumatically so as to change from an open position, in which it is in the retracted state under the effects of suction, to an outspread or closed position in which it tightly seals the body 1 by delimiting a suction chamber 38 inside the latter.

This additional sphincter 36 and this sealing shutter 37 are commanded by a control circuit using two respective electrovalves $EV_5$ and $EV_6$ of the same type as the electrovalves $EV_1$ to $EV_4$.

The direct output of the electrovalve $EV_5$ is connected to the suction circuit 34, while its derivation output $S_2$ is connected to a pressurized fluid circuit 39.

Conversely, the direct output of the electrovalve $EV_6$ is connected to the circuit 39, while its derivation output is connected to the circuit 34.

The suction chamber 38 communicates, via a bore, with a draw measuring circuit 40, considering that by definition the draw of a cigarette filter is the load loss measured at one end of the latter when axially passed through at a standardized rate of 17.5 ml/s, the other end being aired, the filter envelope or jacket being made airtight by means of an encapsulation envelope over its entire length. This measurement is referred to as TFE (Draw of fully encapsulated filter).

The measuring circuit 40 thus comprises a suction pipe 41 fitted with a analog-output differential pressure sensor 42 and connected to a mechanism for generating a static vacuum 43 via a critical flow rate orifice 44 specially calibrated so as to achieve precisely a flow rate of 17.5 ml/s.

The vacuum generator 43 used in this example is of the venturi type which, when fed with a supply of compressed air commanded by an electrovalve $EV_7$, enables suction to be generated.

The entire device is driven by a microcomputer 46 which performs the task of commanding the electrovalves $EV_1$ to $EV_7$ as a function of the measurement cycle, and which manages the data.

The draw measurements (pressures detected by the sensor) are acquired by the microcomputer 46 via an analog-to-digital converter 48.

Specifications such as target values, minima and maxima, alarm thresholds for each of the TPE and TFE parameters, and filter length are entered beforehand into the processing system via the keyboard 49 associated with the microcomputer.

This system processes the data, performs the TPE and TFE display tasks (display 50), compares these values with the minima and maxima, triggers the alarms which are either displayed or audible, and computes the end-of-batch statistics required for production management.

A complete measurement cycle can successively comprise a filter insertion phase, a TPE measurement phase, a TFE measurement phase and an ejection phase.

During the ejection phase, the membrane portions 2 to 5 are brought into the retracted state in order to let the filter pass, while the retention sphincter 36 is disposed in the outspread state. The sealing shutter 37 is then in the open position.

To carry out a TPE measurement phase, the sealing shutter 37 is placed in the closed position so as to make the suction chamber 38 airtight, and the basic sphincter 5 is put into the outspread position so as to partially encapsulate the filter. The membrane portions 2 to 4 are maintained in the retracted state.

A suction phase is then conducted in the measuring circuit 40 so as to obtain a predetermined flow rate, e.g. 17.5 ml/s.

The microcomputer 46 then inputs the TPE value detected by the sensor 42.

The TFE measurement phase can then be carried out by bringing all or part of the membrane portions 4, 3, 2, depending on the length of the filter, to the outspread state in order to completely encapsulate the filter.

The microcomputer 46 subsequently inputs the TFE values detected by the sensor 42, then processes these values, displays them, triggers an alarm if necessary, and stores the results.

The ejection phase comprises stoppage of the suction in the measuring circuit 40, a returning of the membrane portions 2 to 5 and 36 to the retracted state and the sealing shutter 37 to the open position, and the recovery of the filter beneath the body 1.

I claim:

1. A device for measuring the porosity of a filter element, said device using a filter element encapsulating means acting like a sphincter, a means enabling an air flow to be generated through said filter element once said filter element has been encapsulated, and a means enabling measurement of at least one parameter relating to the fluid flow through said filter element, wherein said encapsulating means comprises a succession of encapsulation modules arranged coaxially end to end and each acting like a sphincter, independently of the others, by means of a control means separate from that of the others.

2. The device as claimed in claim 1, wherein in said succession, only a fraction of said encapsulation modules is used depending on the length of said filter element, so as to encapsulate filters of different lengths.

3. The device as claimed in claim 1, wherein each of said encapsulation modules comprises a tubular body whose inner cylindrical wall is lined with an elastic tubular membrane which, along with said wall, delimits an intermediate volume in which the pressure can be modified by a control circuit so that said membrane can be in the following two states:
- a retracted state, retracted towards said wall and providing a cross section of maximum passage,
- an outspread state, spread out towards the center of said body, in which it has a cross section of reduced passage, so as to be able to apply itself against and partially encapsulate a filter element disposed inside said body while it was in the retracted state.

4. The device as claimed in claim 3, wherein the switching from one of said states to the other is achieved by means for admitting, into said intermediate volume, a pressurized fluid or, on the contrary, by means for creating a partial vacuum inside said volume.

5. The device as claimed in claim 3, wherein said tubular body is common to all said encapsulation modules.

6. The device as claimed in claim 5, wherein said different encapsulation modules have elastic tubular membranes disposed end to end and connected to one another, in a tight manner, by means of a multiplicity of annular distance tubes in airtight contact with said tubular body, so as to constitute a succession of intermediate volumes each delimited by said body, a membrane portion and two successive annular distance tubes, each of these volumes being connected to a control circuit separate from that of the others.

7. The device as claimed in claim 6, wherein said intermediate volumes communicate with a distributor mounted on said body, via respective radial bores.

8. The device as claimed in claim 7, wherein said distributor consists in a slide valve formed by a cylindrical tubular sleeve element mounted slidably on said body by means of three tightness seals axially offset so as to delimit two annular chambers of which one is connected to a permanent suction circuit, with the other being connected to a control circuit capable of generating a suction or an airing, or even an injection of pressurized fluid.

9. The device as claimed in claim 1, wherein said encapsulating means further comprises successively after a basic encapsulation module:
- an elastic membrane portion forming an additional sphincter acting as a retaining stop for the filter element when the latter is inserted,
- a sealing shutter susceptible of changing from an open position to a closed position in which it tightly seals the body, by delimiting a suction chamber inside the latter.

10. The device as claimed in claim 9, wherein said suction chamber is connected to a measuring circuit which comprises a suction circuit fitted with a pressure sensor and connected to a mechanism for generating a static vacuum via a critical flow rate orifice.

11. The device as claimed in claim 10, wherein the vacuum generator is of the venturi type and is fed with an air flow commanded by an electrovalve.

12. The device as claimed in claim 10, wherein the said sensor detects values which are acquired by a microcomputer which performs the device control tasks and data management.

* * * * *